United States Patent [19]

Eibl et al.

[11] Patent Number: 5,804,181
[45] Date of Patent: Sep. 8, 1998

[54] PHARMACEUTICAL PREPARATION FOR THE PREVENTION AND TREATMENT OF BLOOD COAGULATION DISORDERS

[75] Inventors: Johann Eibl; Hans Peter Schwarz; Katalin Varadi, all of Vienna, Austria

[73] Assignee: Immuno Aktiengesellschaft, Vienna, Austria

[21] Appl. No.: 452,169

[22] Filed: May 26, 1995

[30] Foreign Application Priority Data

May 27, 1994 [DE] Germany ............................ 44 18 635.5

[51] Int. Cl.$^6$ ..................................................... A61K 38/36
[52] U.S. Cl. .................................. 424/94.1; 514/2; 514/8
[58] Field of Search ........................... 514/1, 8; 424/94.1

[56] References Cited

U.S. PATENT DOCUMENTS 5,143,901  9/1992  Schwerz et al. ........................... 514/12

FOREIGN PATENT DOCUMENTS 0 244 834  5/1987  European Pat. Off. .
0 255 771  2/1988  European Pat. Off. .
0 406 216  6/1990  European Pat. Off. .
WO 93/10261  5/1993  WIPO .
WO 94/17415  8/1994  WIPO .

OTHER PUBLICATIONS

Jane et al., Blood Coagulation and Fibrinolsis 3: 257–261 (1992).

Dahlbäck et al., Proc. Natl. Acad. Sci. USA 90: 1004–1008 (Feb. 1993).

Dahlbäck et al., Proc. Acad. Sci. USA 91: 1396–1400 (Feb. 1994).

*Primary Examiner*—Jeffrey C. Mullis
*Attorney, Agent, or Firm*—Foley & Lardner

[57] ABSTRACT

A pharmaceutical preparation for the prevention and treatment of blood coagulation disorders is described which is characterized in that it comprises Factor V as a native protein, derivative and/or fragment thereof and Protein S in suitable pharmaceutical carrier.

15 Claims, 3 Drawing Sheets

PLASMA SAMPLES:

1. NORMAL
2. MODERATELY IMPAIRED APC - RESPONSE
3. STRONGLY IMPAIRED APC - RESPONSE
4. LACK OF FACTOR V
5 - 9. IMPAIRED APC - RESPONSE IN DIFFERENT DEGREES
10. FACTOR V ABNORMALITY

PHARMACEUTICAL PREPARATION FOR THE PREVENTION AND TREATMENT OF BLOOD COAGULATION DISORDERS

BACKGROUND OF THE INVENTION

The invention relates to a pharmaceutical composition for the prevention and treatment of blood coagulation disorders which comprises Factor V, its derivative and/or fragment and Protein S. Blood coagulation is understood as the process of the conversion of fluid blood into the so-called blood clot which constitutes a gelatinous mass that allows the sealing of damaged blood vessels through plug formation. The conversion of the soluble fibrinogen present in the plasma into the fibrous, gelatinous coagulation material, so-called fibrin, occurs in a multi-step process (the so-called blood coagulation cascade) in which at least 15 different blood coagulation factors, characterized with roman numerals, are involved of which each, when activated, in turn again activates the next respective inactive pre-step. Among these activators are several serine proteinases (such as kallikrein, thrombin, and the activated Factors VII, IX, X, XI and XII). An activated coagulation factor is also characterized with "a" (after the roman numeral). Due to the relatively large number of activation steps in this blood coagulation cascade and the catalytic effect present in each step, a further increase is attained because even with very low amounts of initializing factor a sufficient amount of fibrin is present in as short a time as possible. In addition, the blood cells which are entrapped between the resulting fibrin fibers are involved.

One principally distinguishes between 2 different pathways of activation of blood coagulation Which, however, lead to a common pathway.

The intrinsic blood coagulation pathway relates to the blood coagulation components which normally circulate in the blood and can be introduced when blood comes in contact with non-physiological surfaces, for example with glass or ceramic, wherein both proteins kininogen and kallikrein are involved. Then, the Factors XII, XI, IX and X are activated in succession, whereby in the last named step of the activation of X by IXa, Factor VIII which is absent in the blood disorder hemophilia A is necessary.

In the extrinsic blood coagulation pathway, a tissue factor (tissue factor which is a lipoprotein) is released with the injury of blood vessels and the so-called Factor VII is activated, which both together then activate the above named Factor X. The subsequent common pathway, which is followed thereafter in intrinsic blood coagulation as well as extrinsic blood coagulation, is then the following:

Factor Xa with the help of Factor Va activate prothrombin (Factor II) on the thrombocyte membrane to thrombin, and this, through the cleavage of peptides of fibrinogen (Factor I), releases fibrin monomers which are capable of polymerizing to fibrin fibers. Through activated Factor XIII, cross-linking, and therewith, stabilization of the fibrin fibers, finally results. The intrinsic and the extrinsic blood coagulation pathway are intertwined inasmuch as the activated Factor VII, together with the tissue factor, also activates Factor IX, while for example kallikrein can also stimulate the extrinsic pathway. Aside from the named factors, the presence of phospholipids and calcium, which bind to 4-carboxy-L-glutamic acid groups, is necessary in several steps. The carboxylation of L-glutamate in these proteins is thereby dependent on vitamin K.

The inhibition of blood coagulation occurs through activated Protein C (also a serine proteinase) which proteolytically inactivates the Factors Va and VIIIa. Antithrombin III (a serine proteinase inhibitor) also contributes to the necessary control of blood coagulation by irreversibly inhibiting thrombin and the other involved proteinases. The dissolution of no longer needed blood clots is then brought about by the serine proteinase plasmin which proteolytically cleaves fibrin fibers (see for example Rompp Chemical Encyclopedia, 9th Edition (1989), 463; Rompp Encyclopedia of Biotechnology (1992), 133). Protein C (autoprothrombin II A, Factor XIV) is a vitamin K dependent glycoprotein which is synthesized in the liver and circulates in the plasma as an inactive zymogen in a concentration of 4 $\mu$g/ml. It is transformed on the vessel wall surface (the endothelium) by the thrombin-thrombomodulin complex into the active serine proteinase (activated Protein C, APC), and possesses profibrinolytic properties as activated Protein C (active serine protease). It also functions as an anti-coagulant because it cleaves Factor Va, the cofactor for the Factor Xa induced prothrombin activation (thrombin formation), and Factor VIIIa, the cofactor for the Factor IXa induced Factor X activation, through proteolysis.

Aside from calcium ions and phospholipids, a further protein, so-called Protein S (molecular weight 84,000) functions as a cofactor which, however, possesses no protease activity itself; Protein S functions non-enzymatically as a cofactor for the anti-coagulatory and profibrinolytic properties of Protein C. Native plasma contains between 25 $\mu$g and 30 $\mu$g of Protein S per ml, wherein Protein S is present in different forms. The cofactor activity is attributed to the free form of Protein S, while a complex of Protein S with C4b binding protein shows no activity.

It is known that activated Protein C extends the plasma coagulation time in a dosage-dependent manner. However, in a Protein S deficient plasma, activated Protein C can not properly exercise its function, but rather, the effect of activated Protein C is only improved by the addition of Protein S. The effect of Protein S on activated Protein C is described for example in Blood Coagulation and Fibrinolysis 3 (1992), 257 to 261. It was observed that an increase of the Protein S concentration leads to a linear amplification of the anti-coagulant effect of activated Protein C. Thereby, it was found that the concentration of Factor Va plays no role. In Factor V deficient plasma, it was observed that the anti-coagulant effect of activated Protein C was relatively low. However, through the addition of Protein S, the insufficient effect of activated Protein C could be improved.

A number of reasons can be given for the decreased effect of activated Protein C. In Proc. Natl. Acad. Sci. (PNAS) USA 90 (1993), 1004 to 1008, a weak anti-coagulant response of the activated Protein C in a number of patients is described. However, these patients possessed no detectable deficiency of Protein C, Protein S, antithrombin III, plasminogen and other relevant blood components. Therefore, it was assumed that a previously unknown cofactor for Protein C may be responsible for this clinical picture. A deficiency of this cofactor for activated Protein C can, therefore, lead to thromboembolic disease states.

It was found that a corresponding cofactor activity is associated with the coagulation factor V. In Proc. Natl. Acad. Sci. (PNAS) USA 91 (1994), 1396 to 1400, an anti-coagulant cofactor activity for the activated Protein C is attributed to Factor V.

Factor V is a $\beta$-globulin with a molecular weight of 330 kD which is activated through limited proteolysis by thrombin and inactivated by activated Protein C. Thereby, specific fragments result. Factor V is, in its active form, a component of the prothrombinase complex (comprising Factor Xa, Factor Va, phospholipid, calcium ions for the activation of prothrombin) which is responsible for thrombin formation and, therewith, for blood coagulation. Therewith, Factor V is itself considered to be a procoagulant coagulation factor. The inborn and inherited deficiency of Factor V is associated with a tendency to bleed that is similar to hemophilia.

WO-A-93/10261 describes methods for the determination of blood coagulation disorders which are based on a weak effect of activated Protein C.

A further method for the determination of the sensitivity of a blood and/or plasma sample for activated Protein C ("APC-sensitivity", "APC-response") is described in US application Ser. No. C8/160877. Accordingly, the Factor VIII activity of a sample, to which activated Protein C was added, is determined in a simple manner by means of a chromogenic assay based on Factor Xa and is set in relation to the Factor VIII activity that is measured without addition of activated Protein C. The larger the obtained ratio is, the higher the sensitivity towards activated Protein C.

SUMMARY OF THE INVENTION

The object of the present invention is to make available a pharmaceutical preparation with which the effect of activated Protein C can be normalized or amplified.

The object is solved with the subject matter of the present invention.

Subject matter of the invention is a pharmaceutical composition for the prevention and treatment of blood coagulation disorders which is characterized in that it comprises Factor V as a native protein, derivative and/or fragment thereof and Protein S in a suitable pharmaceutical carrier (APC-enhancer).

Preferred embodiments of this composition include pharmaceutical preparations for the prevention and treatment of blood disorders that comprise Factor V and Protein S. The preparation can be substantially free of activated factor V, and can further comprise Protein C and/or activated Protein C.

Further subject matter is the use of Factor V as a native protein, its derivatives and/or fragments in combination with Protein S and/or a Protein S containing pharmaceutical composition for the prevention and/or treatment of blood coagulation disorders.

Preferred embodiments thereof methods for the prevention and treatment of blood coagulation disorders, comprising the step of administering to a patient Factor V and Protein S. The method can include administration of the Factor V that is substantially free from activated Factor V. The method can further include the step of administering at least one protein selected from the group consisting Protein C and activated Protein C. Additionally, according to the method, Factor V and Protein S are administered simultaneously or consecutively in any order.

Further subject matter is the use of Factor V as a native protein, its derivatives and/or fragments in combination with Protein S for the preparation of a pharmaceutical composition for the prevention and/or treatment of blood coagulation disorders.

Preferred embodiments thereof methods for the prevention and treatment of blood coagulation disorders, comprising the step of administering to a patient a pharmaceutical composition comprising Factor V and Protein S. The method can include administration of the pharmaceutical composition that is substantially free from activated Factor V. The pharmaceutical composition of the method also can include a protein selected from the group consisting Protein C and activated Protein C.

The application of Factor V, its derivative and/or fragment and Protein S or Protein S containing preparations for the prevention and treatment of blood coagulation disorders can thereby occur together, simultaneously (but separate from another) or also consecutively and in any order.

Further subject matter of the invention is also a set (kit) for the production of a pharmaceutical composition according to the invention which comprises, in 2 separate containers, Factor V as a native protein, derivative and/or fragment, and, in one or more further containers, Protein S, wherein the containers can optionally contain still further pharmaceutically acceptable carriers and diluents in combination with the active ingredients, and/or, separate therefrom in a separate container.

In a preferred embodiment, the composition according to the invention is substantially free from activated Factor V. In a further suitable embodiment, the composition according to the invention, additionally comprises Protein C and/or activated Protein C, aside from Factor V as a native protein, derivative and/or fragment. Suitably, in a direct application or use of the individual components, Protein C and/or activated Protein C can still be applied or used for example for the production of a pharmaceutical composition together, simultaneously, before or after the application or use.

The preferred ratio of Factor V as a native protein, derivative or fragment (Factor V active substance) to Protein S amounts to 1:2 to 1:100 according to the invention, most preferably 1:5 to 1:50 (molar ratio).

Appropriately, the composition according to the invention comprises Factor V as a native protein, derivative or fragment thereof in a manner and amount which has no procoagulatory activity.

According to the invention, thromboembolic disease states are especially understood as blood coagulation disorders.

DETAILED DESCRIPTION OF PREFERRED EMBODIMENTS

Figure 1:
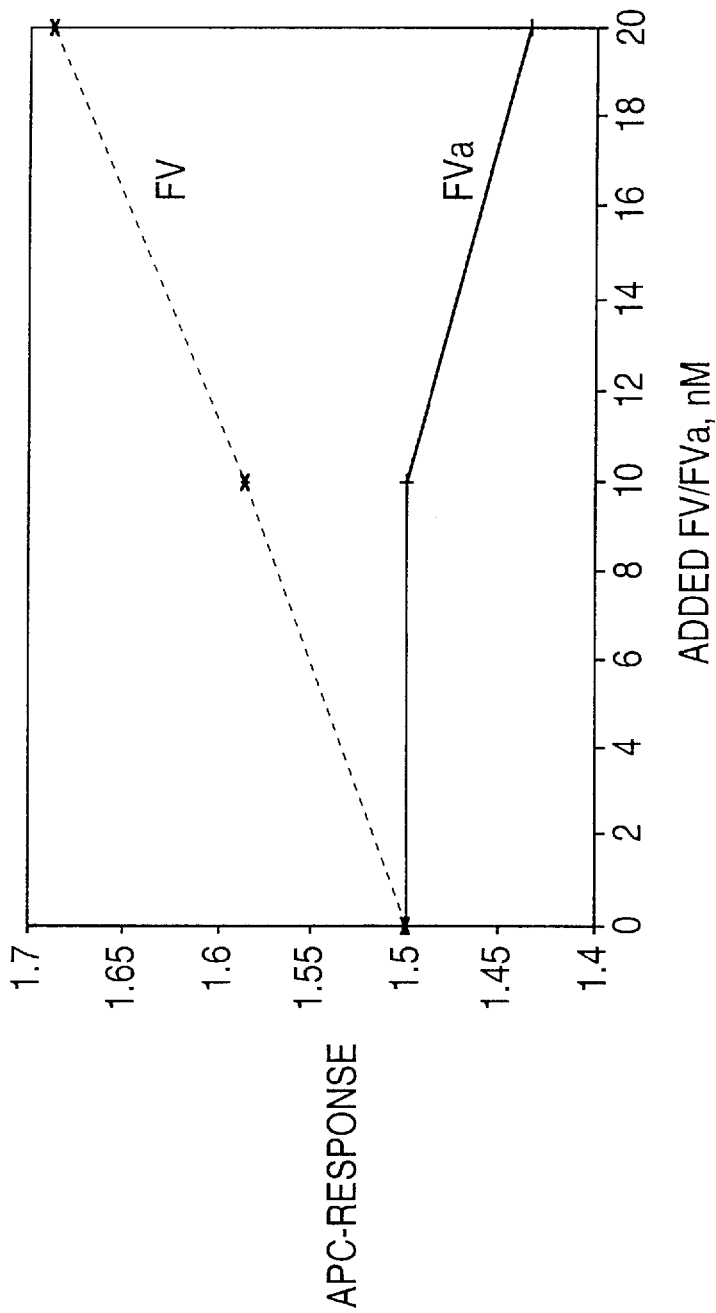
FIG. 1 depicts the effect of factor V and factor Va on the inactivation of factor VIII by activated protein C according to Example 1.
Figure 2:
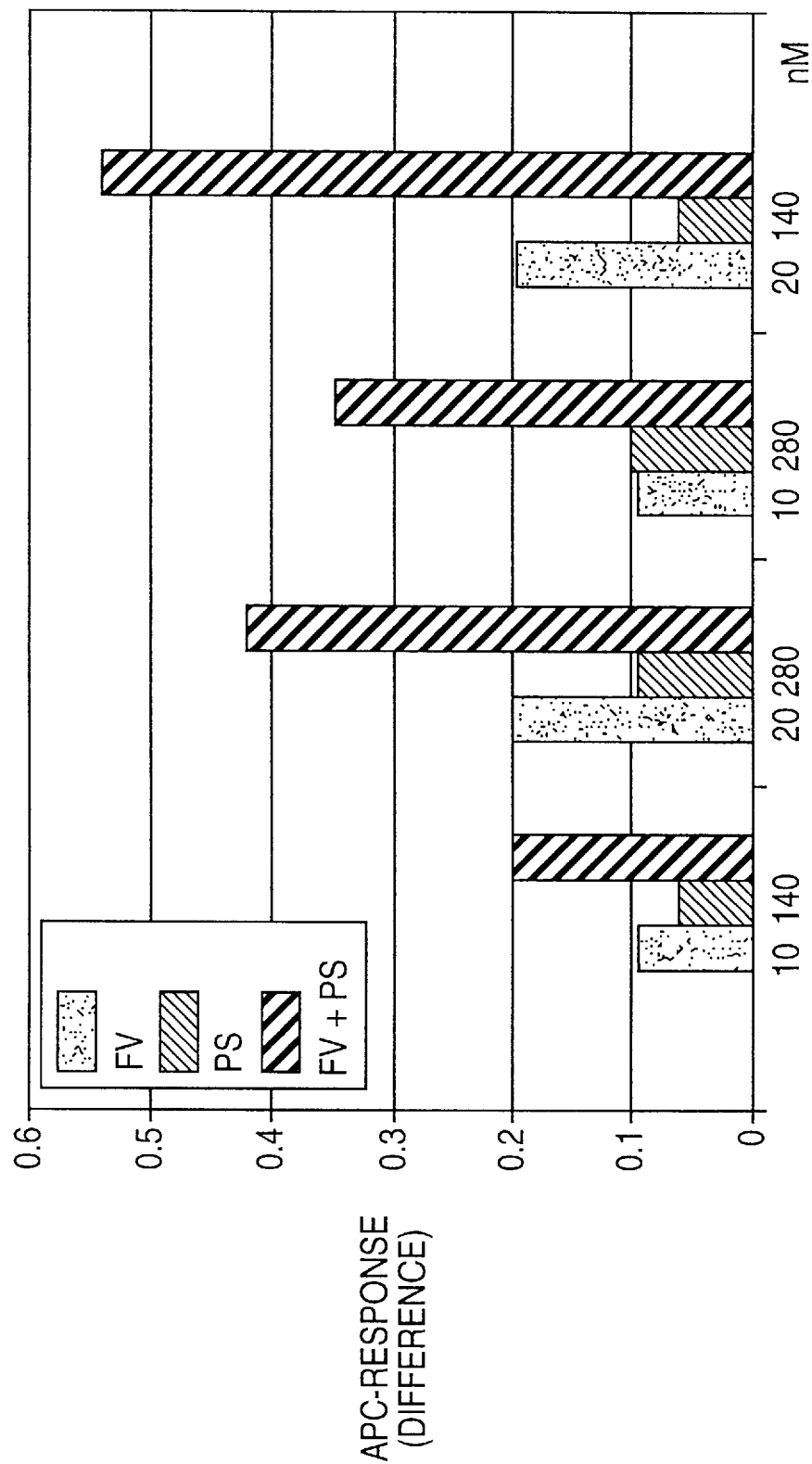
FIG. 2 depicts the effects of factor V and protein S on the inactivation of factor VIII by activated protein C according to Example 1.
Figure 3:
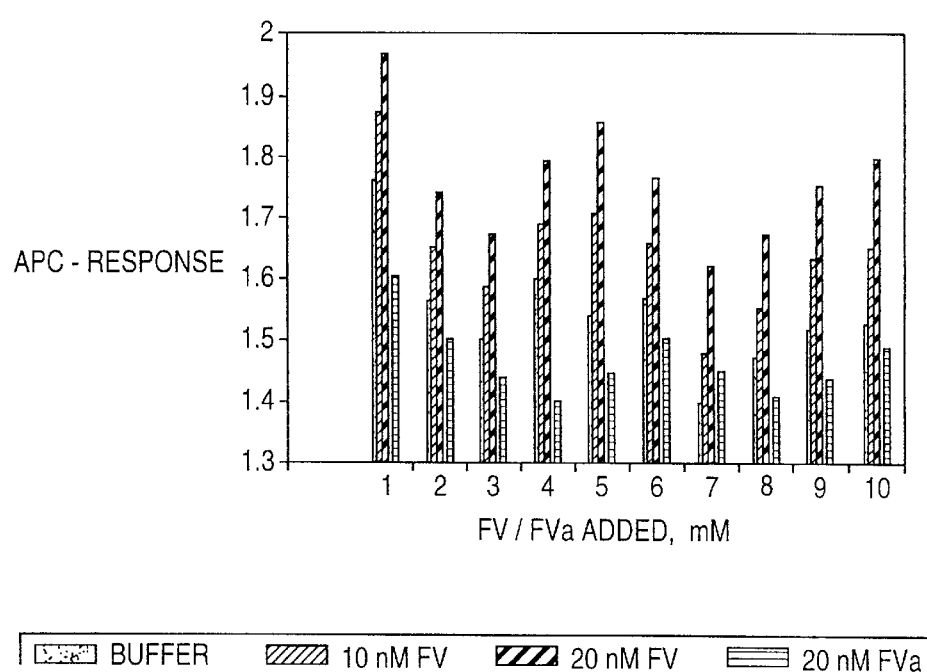
FIG. 3 depicts the effect of factor V and factor Va on the activated protein C response of various test plasmas according to Example 1.

It has now been shown that blood coagulation disorders, especially thromboembolic disease states can be effectively prevented, or that these can be effectively treated, with the pharmaceutical preparations according to the invention which comprise a combination of Factor V and Protein S.

It was found that a synergistic effect of Protein S and Factor V is present on the "APC-sensitivity" of a sample (measured according to U.S. Ser. No. 08/160877).

Surprisingly, it has been shown that the anti-coagulant effect of activated Protein C can be substantially increased by the composition according to the invention, i.e., by the presence of the cofactor Protein S and the coagulation factor V in the form of a native protein, derivative and/or fragment thereof.

These results must be considered as surprising in more than one respect: in one respect, the effect of activated Protein C in a Factor V deficient plasma could be normalized by the addition of Protein S alone (see Blood Coagulation and Fibrinolysis, supra); on the other hand, at most an additive effect of Protein S and Factor V could be expected regarding an APC cofactor activity of Factor V. Because Factor V also possesses procoagulant properties, not only an agonistic but also an antagonistic effect on blood coagulation must possibly have been expected.

Appropriately, the composition according to the invention is sustantially free of activated Factor V. Thereby, an undesired procoagulant activity is prevented. Furthermore, it was determined that an amplified effect of activated Protein C by Factor V is found only when the protein is present in its inactive form, its derivatives and/or fragments. The activated Factor V has, on the other hand, an opposite effect. Activated Protein C is surprisingly inhibited by Factor Va, shown on the inactivation of Factor VIIIa by activated Protein C in the presence of Factor Va. Therefore, in the production of the pharmaceutical composition according to the invention, particular attention should be paid that a non-activated Factor V or a suitable derivative and/or fragment thereof is selected in a manner and amount which has no procoagulatory effect. A fragment of Factor V which is cleaved in the activation of the protein (so-called activation peptide) is especially suitable as a fragment.

The portion of activated Factor V in the total amount of Factor V in the composition according to the invention amounts to preferably less than 50 percent by weight, and especially less that 30 percent by weight. In a particular preferred embodiment, the composition is therefore produced in such a way, for example in the presence of a protease inhibitor, that the presence of activated Factor V can be extensively excluded.

The composition according to the invention can additionally comprise Protein C and/or activated Protein C; thereby a simultaneous treatment of an inborn or acquired Protein C deficient state is possible.

The composition according to the invention can be produced by using proteins isolated from blood plasma or from recombinant proteins and/or polypeptides (also Protein S polypeptides with an APC cofactor activity).

Proteins of this type are either obtainable commercially or can be produced according to customary methods (see for example EP-A-0406216, EP-A-0255771, EP-A-0244834).

Independently of whether the proteins are isolated from blood plasma or produced by using a cell culture method, it is suitable to use starting materials and/or proteins which were treated in the customary way for the inactivation of infectious agents, such as for example viruses, viroids and virions.

The pharmaceutical composition according to the invention is produced, when necessary, by using suitable adjuvants carriers and/or additives customary for these types of preparations which are safe, especially for administration to humans. The adjuvants carriers and/or additives used are determined especially by the intended mode of administration. The pharmaceutical compositions can be present in customary forms for this, for example as tablets, coated tablets, capsules, suppositories, syrups, injection solutions, infusion solutions, etc.; preferably they are present in a form suitable for intravenous administration.

In an embodiment, the composition according to the invention can also be made available as a set (kit) in which the components are kept separately from each another, and are first combined at the time of application. A set according to the invention for the product,on of the pharmaceutical composition comprises, for example, in a container (a), Factor V, its derivative and/or Fragment, and in a second container (b), Protein S, and, the optional adjuvants, carriers and/or additives for the production of the pharmaceutical composition according to the invention can be contained together or as individual components distributed in one of the containers (a) and/or (b), or also in a further additional container (c).

The mixture of the components of the containers (a), (b) and optionally (c) can occur in a customary manner and suitably occurs shortly before the application.

In an embodiment of the invention, it is also possible to individually apply the individual active ingredients of the pharmaceutical composition according to the invention, namely either simultaneously or in any order in succession. In this way for example, Factor V, its derivative and/or fragment can be applied simultaneously together with the component Protein S, or Factor V, its derivative and/or fragment can be applied at first and thereafter Protein S, or also in the reversed order. Thereby, the administration of each of the components suitably occurs, especially dependent on the application, in the presence of an adjuvant, carrier and/or additive suitable therefor.

The invention is more closely illustrated in the following Example without being limited to it.

Example 1

Method for the determination of APC-sensitivity (APC-response) (according to U.S. Ser. No. 08/160877)
I. Basic method for measurement of the APC-response in plasma
50 μl plasma or sample - diluted 1/20 in FVIII dilution buffer (Immunochrom® FVIII:C, Immuno AG)
50 μl buffer or APC (2 U/ml)
100 μl reagent A (phospholipid, Immunochrom® FVIII:C, Immuno AG)
100 μl reagent B (activators+FX, Immunochrom® EVIII:C, Immuno AG)
5 min/37° C. incubation
200 μl chromogenic substrate (containing EDTA, in order to stop further Xa activation) 4 mmol/l $CH_3OCO$-D-CHA-GLY-ARG-pNA-AcOH (Immunochrom® FVIII:C, Immuno AG) diluted 1:3 in Factor VIII reaction buffer (Immunochrom® FVIII:C, Immuno AG)
5 min/37° C. incubation
the reaction is stopped with 100 μl acetic acid (50%)
The extinction is measured at 405 nm (A405)
Result: Ratio of A405 (buffer) to A405 (APC)=APC response The effect of different additives on the APC response was also examined according to this method as follows.
The plasma samples to be examined were mixed with buffer (9+1), or Protein S, or FV or FVa, or with some other reagent which could have an influence on the FVIII inactivation influenced by APC. The plasma sample containing additives is diluted altogether 1/20 and respectively tested without or with APC addition in order to determine the ratio (APC-response).
Ia. Method for measuring the effect of APC on purified Factor VIII (FVIII)
Proceeding according to the same method above, but instead of the plasma probe, purified FVIII was measured. The final concentration of FVIII amounted to approximately 0.05 U/ml. When the effect of one or several other factors was tested, 1 U/ml FVIII in the ratio 9+1 or 8+1+1 was premixed with the additives or buffers, diluted altogether 1/20 and tested with or without APC addition. According to this system, it is also possible to vary the FVIII concentration and to use dilutions other than the 1/20 dilution and to vary the APC concentration.

The results obtained according to the methods of the above example 1 are recorded as follows in the form of Figures.

We claim:

1. A pharmaceutical preparation for the prevention and treatment of thrombolic or thromboembolic disorders comprising Factor V and Protein S.

2. A pharmaceutical preparation according to claim 1, wherein said preparation is substantially free of activated Factor V.

3. A pharmaceutical preparation according to claim 1 comprising at least one protein selected from the group consisting of Protein C and activated Protein C.

4. A pharmaceutical preparation according to claim 1, wherein the Factor V has no procoagulatory activity.

5. A pharmaceutical preparation according to claim 1, wherein the molar ratio of Factor V to Protein S is from 1:2 to 1:100.

6. A pharmaceutical preparation according to claim 1, wherein the molar ratio of Factor V to Protein S is from 1:5 to 1:50.

7. A kit for the prevention and treatment of thrombolic or thromboembolic disorders, comprising a first container (a) comprising Factor V in a pharmaceutically acceptable carrier, and a second container (b) comprising Protein S in a pharmaceutically acceptable carrier.

8. A method for the prevention and treatment of thrombolic or thromboembolic disorders, comprising the step of administering to a patient Factor V and Protein S.

9. A method according to claim 8, wherein Factor V and Protein S are administered simultaneously or consecutively in any order.

10. A method according to claim 8, wherein the Factor V is substantially free from activated Factor V.

11. A method according to claim 8, wherein said method further comprises the step of administering at least one protein selected from the group consisting Protein C and activated Protein C.

12. A method for the prevention and treatment of thrombolic or thromboembolic disorders, comprising the step of administering to a patient a pharmaceutical composition comprising Factor V and Protein S.

13. A method according to claim 12, wherein the pharmaceutical preparation is substantially free of activated Factor V.

14. A method according to claim 12, wherein said pharmaceutical composition further comprises at least one protein selected from the group consisting of Protein C and activated Protein C.

15. A method according to claim 12, wherein the pharmaceutical preparation has a molar ratio of Factor V to Protein S from 1:5 to 1:50.

* * * * *